US012661002B2

(12) United States Patent
Rassi Gabriel

(10) Patent No.: US 12,661,002 B2
(45) Date of Patent: Jun. 23, 2026

(54) PREFERENTIAL VISUAL ACUITY TEST CABIN

(71) Applicant: Luis Alexandre Rassi Gabriel, Goiânia (BR)

(72) Inventor: Luis Alexandre Rassi Gabriel, Goiânia (BR)

( * ) Notice: Subject to any disclaimer, the term of this patent is extended or adjusted under 35 U.S.C. 154(b) by 1227 days.

(21) Appl. No.: 17/618,777

(22) PCT Filed: Jul. 29, 2019

(86) PCT No.: PCT/BR2019/050302
§ 371 (c)(1),
(2) Date: Jul. 5, 2022

(87) PCT Pub. No.: WO2020/248029
PCT Pub. Date: Dec. 17, 2020

(65) Prior Publication Data
US 2022/0322929 A1 Oct. 13, 2022

(30) Foreign Application Priority Data
Jun. 13, 2019 (BR) .................... BR102019012081-9

(51) Int. Cl.
*A61B 3/032* (2006.01)
*A61B 3/00* (2006.01)
*E04H 1/12* (2006.01)

(52) U.S. Cl.
CPC ............ *A61B 3/032* (2013.01); *A61B 3/0008* (2013.01); *A61B 3/0083* (2013.01); *E04H 1/12* (2013.01)

(58) Field of Classification Search
None
See application file for complete search history.

(56) References Cited

U.S. PATENT DOCUMENTS 9,259,145 B2 * 2/2016 Cabeza Guillen ..... A61B 3/028
2005/0125891 A1 6/2005 Stratmann
(Continued)

FOREIGN PATENT DOCUMENTS

CN 205378090 U 7/2016
JP H03202562 A 9/1991

OTHER PUBLICATIONS

International Search Report for corresponding International Application No. PCT/BR2019/050302 dated Oct. 31, 2019.
(Continued)

*Primary Examiner* — Sharrief I Broome
*Assistant Examiner* — Journey F Sumlar
(74) *Attorney, Agent, or Firm* — McDonald Hopkins LLC

(57) ABSTRACT

A booth, for using the Teller technique to quantify visual acuity, irrespective of a patient's verbal ability booth comprises a modular structure, making up an isolated environment for the patient to perform the acuity test through the reading of Teller cards. The patient is accommodated in a visualization area at the central portion of a movable wall sliding via wheels on rails installed on the ground and ceiling by profiles. The modular structure presents a white and opaque tone, as well as its own lighting which is controlled and proper according to the test, in front of a movable wall and coplanar to a rear wall of booth. The movable wall sliding effects the distance adjustment between the patient and the visualization area cards where the minimum distance is equivalent 38 centimeters and the maximum distance is 55 or 84 centimeters as accuracy dictates, according to the patient's features.

4 Claims, 4 Drawing Sheets

(56)         References Cited

U.S. PATENT DOCUMENTS

| | | | |
|---|---|---|---|
| 2005/0225720 A1* | 10/2005 | Ridings | A61B 3/032 |
| | | | 351/200 |
| 2006/0116555 A1 | 6/2006 | Pavlidis et al. | |
| 2009/0143652 A1 | 6/2009 | Warburton et al. | |
| 2010/0033678 A1* | 2/2010 | Foster | A61B 3/10 |
| | | | 351/200 |
| 2014/0253707 A1* | 9/2014 | Gangadhar | G02C 13/003 |
| | | | 382/100 |
| 2015/0109577 A1* | 4/2015 | Haddadi | G02C 13/003 |
| | | | 351/204 |
| 2017/0311793 A1* | 11/2017 | Green | A61B 3/113 |

OTHER PUBLICATIONS

Preliminary International Report on Patentability for corresponding Internaional Application No. PCT/BR2019/050302 dated Oct. 31, 2019.

* cited by examiner

PREFERENTIAL VISUAL ACUITY TEST CABIN

This application is a 371 National Stage Application of International Application No. PCT/BR2019/050302 filed on Jul. 29, 2019, entitled, "PREFERENTIAL VISUAL ACUITY TEST CABIN", that claims priority to Brazilian Application No. BR102019012081-9, filed on Jun. 13, 2019, the contents of each of which are incorporated herein by reference in their entireties.

TECHNICAL AREA

This patent of invention discloses a booth for a visual acuity test, preferably in the type performed to quantify the visual acuity of a patient, irrespective of the patient's verbal information. Preferably, the "Teller" technique is used. The Teller technique is best practiced in a booth for the testing of visual acuity installation in such environments as offices and clinics staffed by specialized professional. Said booth features a sliding wall, which provides spacing adjustment between the 'Teller' card and the patient accommodated within the cabin according to the exam specifications and the physical features of each patient. Additionally, the construction of the booth allows the administrator of the test to block visual influences which may divert the attention of the patient. Together these aspects allow for a test having better accuracy than other widely available visual acuity tests.

HISTORY OF TECHNIQUE

It is known that visual acuity, basically deals the capacity of the eye to distinguish spatial details, (i.e., to identify the contour and shape of objects), and is often measured in such patients as children in pre-verbal phase, illiterate children with delayed neuropsychomotor development, bearers of cognitive-motor impairment, bearers of encephalic tetraplegic lesions, and patients without speech, among others. the realization of preferred eye acuity tests is necessary, which are proper for each patient's conditions.

The principle of visual acuity is based on the fact that human beings naturally prefer to look at something that exhibits some detail, instead of visualizing areas presenting no details. For example, upon viewing a board, an individual will pay attention to whatever particularities are present in the board, however small they might be.

One of the best used visual acuity test types the Teller test, which is based on "Teller" acuity cards, comprising rectangular plates with neutral tone, where a set of contrasting stripes are presented. Standard visual acuity tests utilize recognition visual acuity, which uses standard line tests. Such tests are not effective in examining infants and pre-verbal children, common candidates for the Teller test. The Teller test instead tests resolution (grating) acuity measured in cycles per centimeter. This measure is applied to the distance between paddles slid progressively closer to one of the side edges of the plate. Said card further presents a central orifice that features an eye, through which the professional assesses the patient's reactions.

During a Teller test, a professional places the rectangular plate a distance that, according to the rules of such a test, might reach 84, 55, or 38 cm from the patient's eyes, so as to expose the card provided with contrasting stripes turned to the patient.

The detail is localized solely one one of the halves of the card face turned to the patient. If the patient perceives such a detail, the professional will certify said fact by observing through the card orifice whether or not the patient looked at the detail. Thus, if the patient has seen the detail in the first card, one passes to the second card and so on, as he continues to look to the side containing the details. At the time the patient no longer looks at the detail, his visual acuity is noticed to be correspondent to the last card in which he was able to notice the detailing.

In order to perform the test, the professional needs to hold the card with the hands, at the height of patient's eyes. The card should be positioned at the height of the professional's eyes, which leads to instability of the card.

Another concern when using the Teller method is external distractions. For example, the hands of the professional, while he was holding the card, may cause the patient to deviate his glance, removing his focus from the set of contracting stripes. This it difficult for the professional to reach a precise diagnosis with respect to the visual acuity test.

ANALYSIS ON THE CURRENT TECHNIQUE STATUS

In research performed in specialized data bases, a document concerning the visual acuity test Chinese Patent No. CN205378090 was found. A portion of the reference germane to the present innovation is reproduced below.

"The utility model discloses a teller looks quick synchronous video system of card inspection arranges in by the person of examining position dead ahead eyesight board, on the eyesight board with be equipped with by the person of examining position parallel and level department leading video camera, with is watched attentively the department by the person of examining position by the person's of examining sight and be equipped with test-card locating place the eyesight backboard is equipped with video recording customer end, top to the quilt person of examining position below department and is equipped with the player of recording a video in step, the video recording customer end with record a video in step between the player through the image transmission line connection, eyesight board top orientation is equipped with the connecting rod by the position level of the person of examining position, the connecting rod tip moves towards downwards and is equipped with rear-mounted video camera by the person of examining position, rearmounted video camera passes through the connecting wire and is connected with the player of recording a video in step, there are the USB interface in image transmission line and the player host computer surface in contact that records a video in step department. Only need open the video recording customer end during operation, the instruction need be carried out the infant that teller looked quick card inspection and sits at the assigned position, and this instrument can be examined all actions of infant according to inspection doctor demand in situ observation and record opening the back, and does not need other special apparatuses to help, and is not only quick convenient but also objective accurate." (sic)

Despite belonging to the same field of endeavor as the present innovation, the pertinent paragraph of the above cited reference presents none of the features of the object now improved.

OBJECTS OF THE INVENTION

An objective of this innovation is to disclose a booth for a preferred visual acuity test, wherein a booth makes up an environment for the patient to perform the preferred activity test through the reading of Teller cards, which in turn are placed within a visualization area foreseen at the central portion of a sliding movable wall on rails installed from the ground to the ceiling of a cabin, thus making it possible to adapt the distance of cards with respect to the patient's eyes and according to respective limitations.

Another objective of this innovation consists in the fact that the booth comprises a neutral and isolated environment for the patient to perform the acuity test, thus eliminating possible external distractions and ensuring a precise diagnosis.

Another aspect of the present innovation is that the area for card visualization, within the sliding movable wall, supports the cards in a stable form.

Another objective of the present innovation is to present a booth with fixed and controlled lighting, so as to provide a better visualization of the cards during the performance of the visual acuity test.

For short, the utilization of the booth provides a substantial increase in accuracy, reliability and reproducibility of preferred visual acuity tests.

DESCRIPTION OF FIGURES

In order to complement this description, and to facilitate a better understanding of the features of the present innovation, and according to a preferred practical performance of the same, an attached description follows with a set of drawings. The drawings are meant to exemplify the functionality of the present innovation but are not intended to show every aspect thereof.

DETAILED DESCRIPTION

Figure 1:
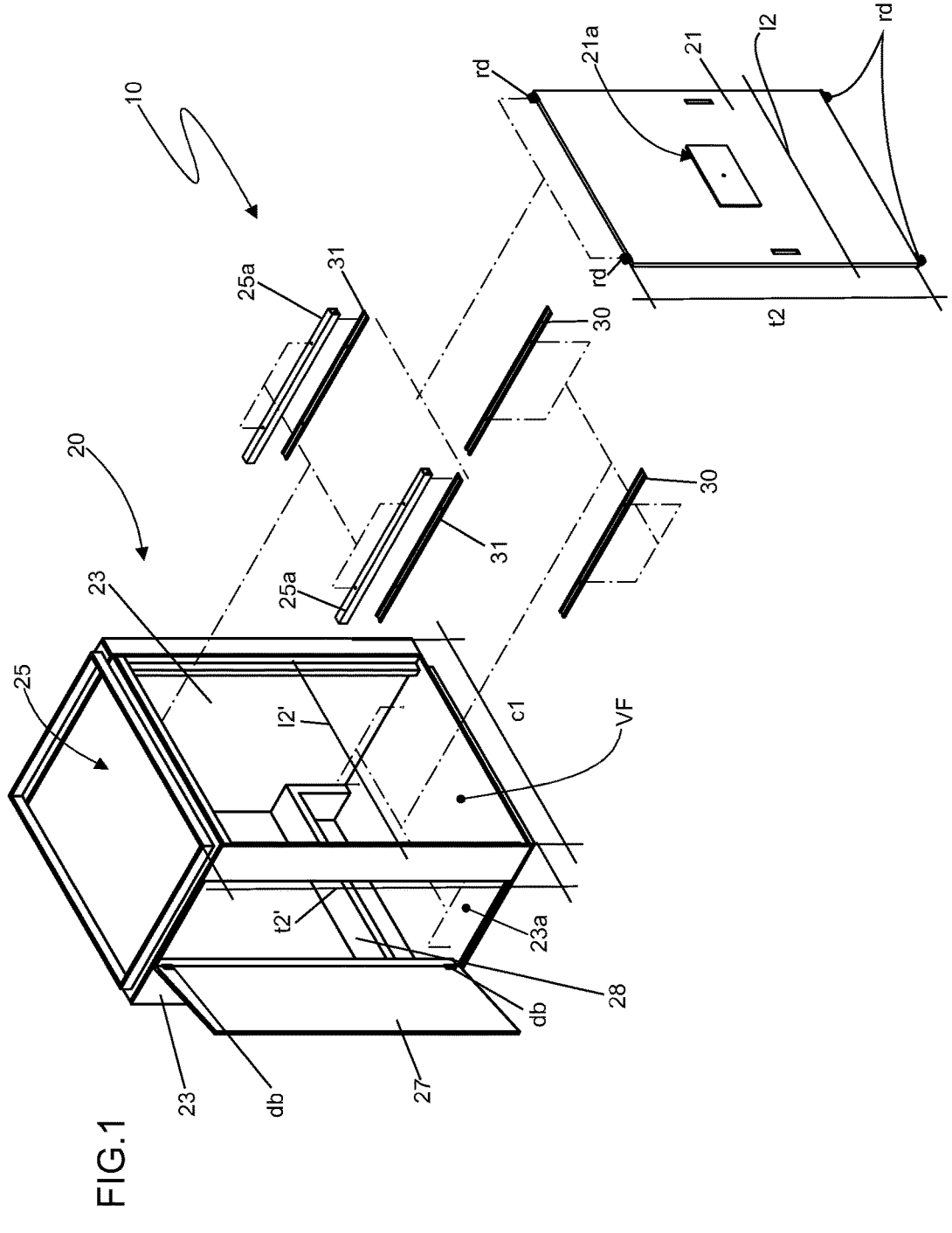
FIG. 1 presents an exploded perspective view of the structure making up the mentioned booth.
Figure 2:
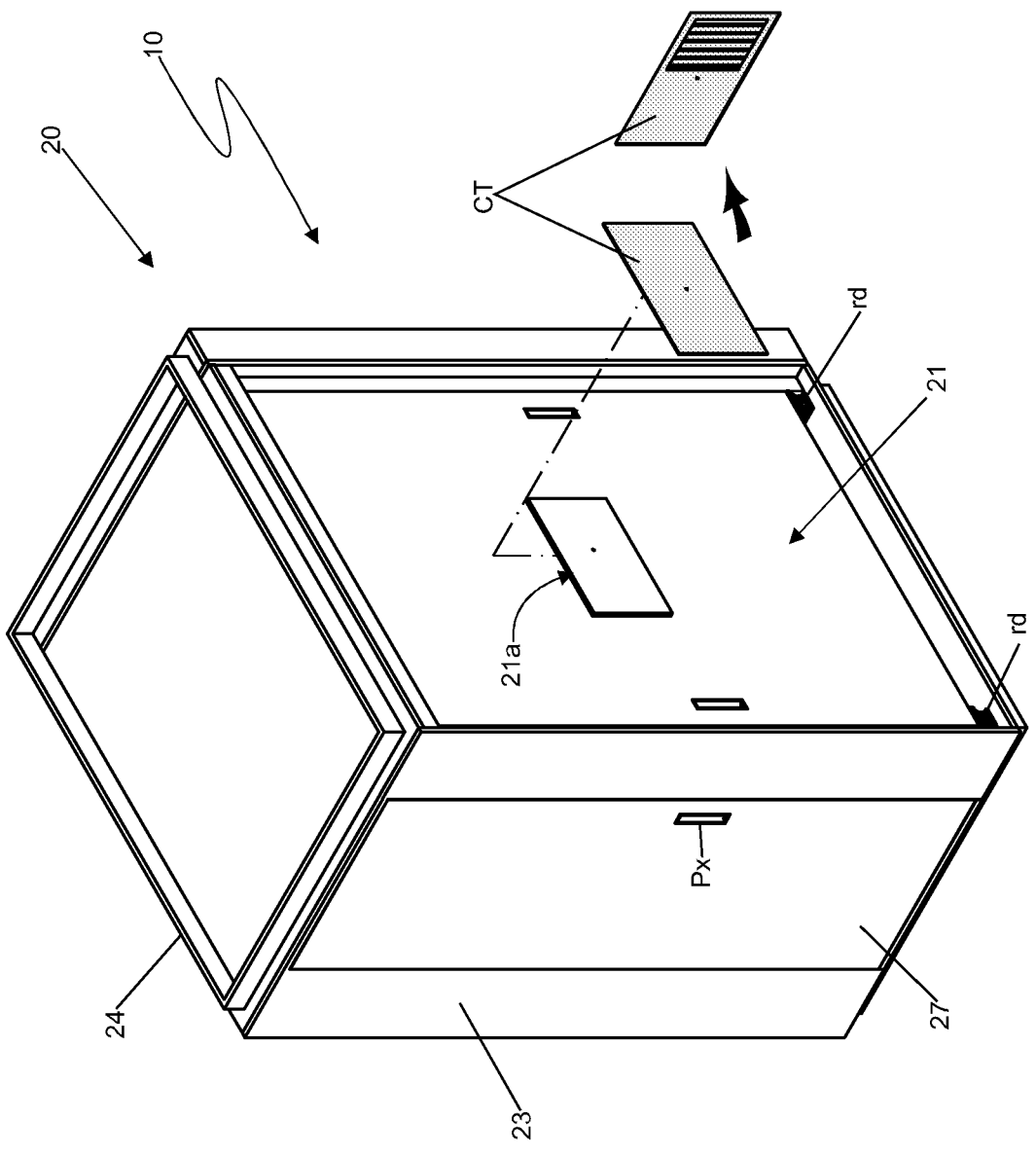
FIG. 2 reveals a perspective view of the assembled cabin.
Figure 3:
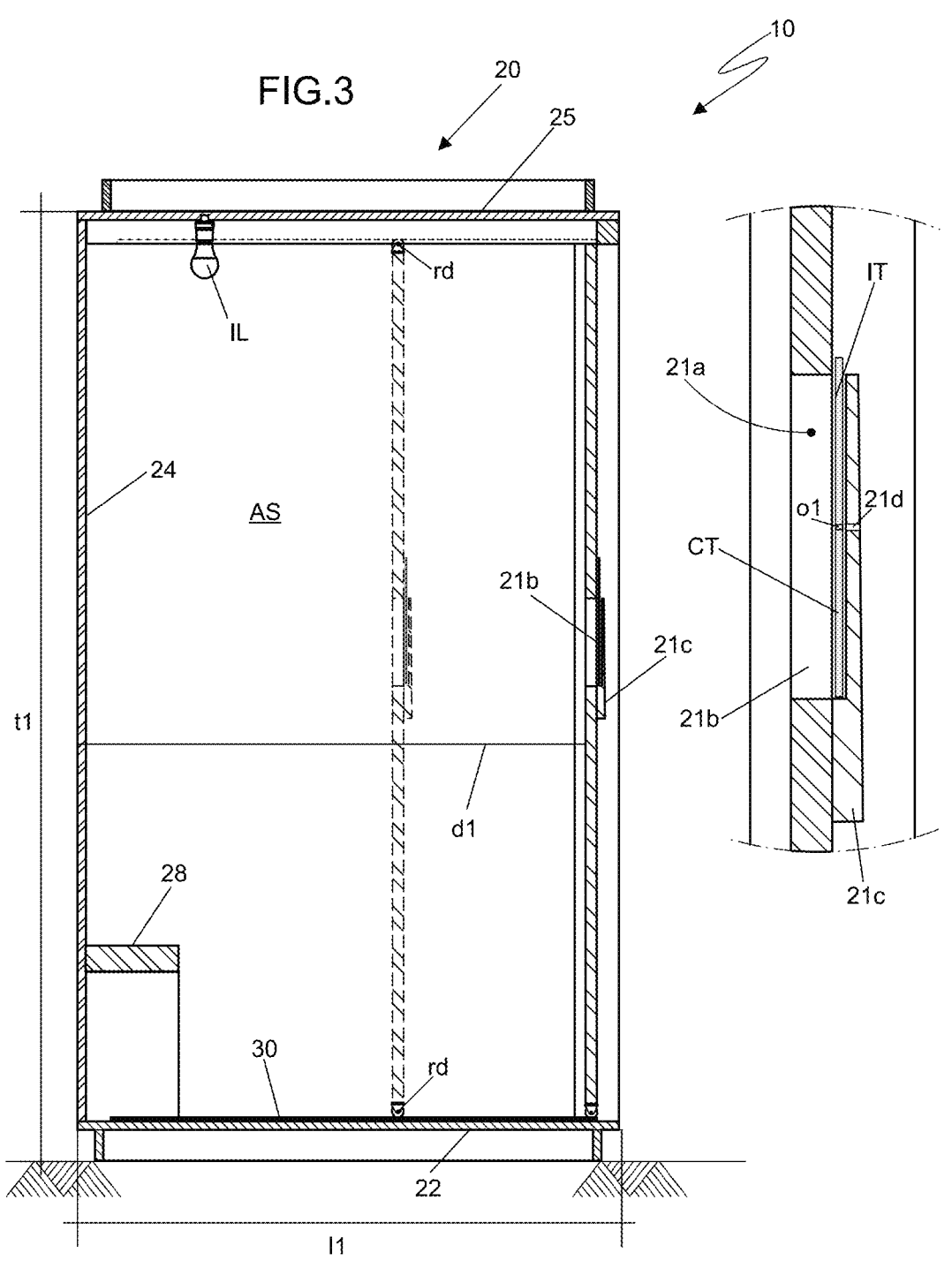
FIG. 3 shows a longitudinal view (AA), of the former figure, with greater detail.
Figure 4:
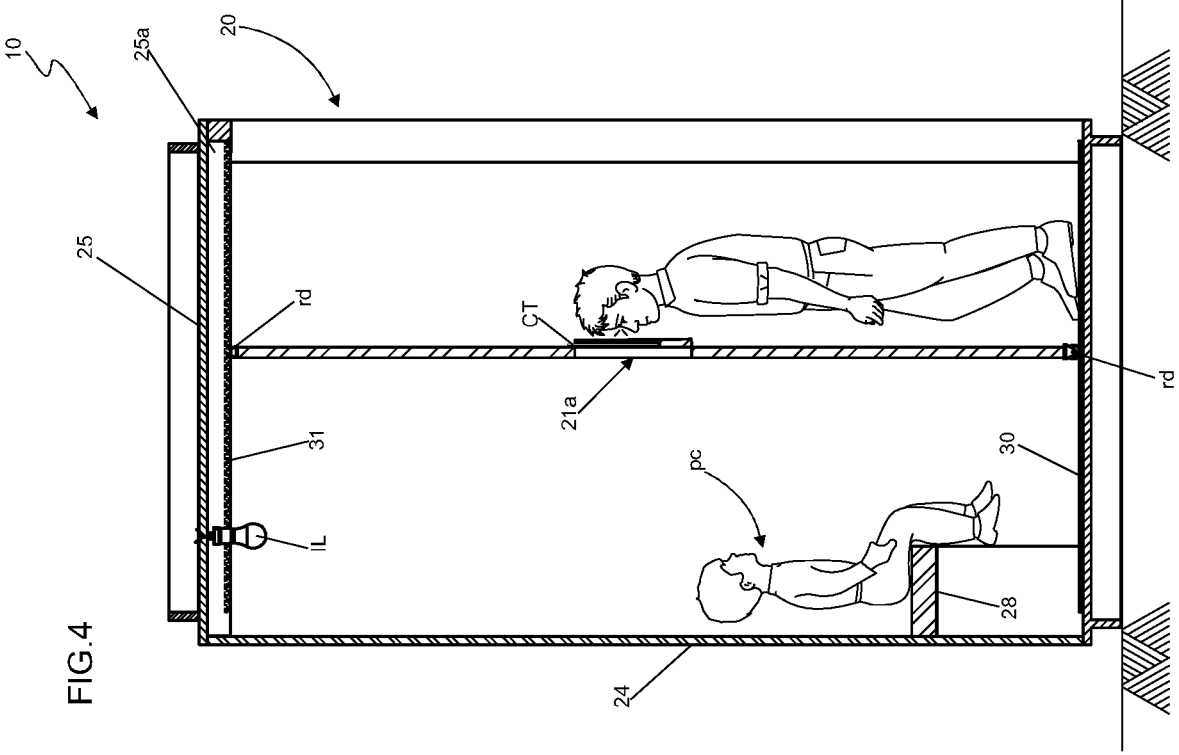
FIG. 4 represents a longitudinal view (AA), illustrating the sliding of the movable wall, when the proper distance adjustment for the performance of the preferred acuity test is made.

With respect to the illustrated drawings, the present innovation is directed toward "A BOOTH FOR THE PREFERRED VISUAL ACUITY TEST". The innovation discloses a booth (10) for use in quantifying the visual acuity irrespective of the patient's verbal information (pc) by means of the Teller technique in such environments as offices and clinics, by a specialized professional.

According to this invention, said booth (10) comprises a modular structure (20) made in wood, drywall, PVC or another type of material, in a way to make up an isolated environment (AS) for the patient (pc) to perform the preferred acuity test through the reading of Teller cards (CT) laid out in the visualization area (21*a*) visible through the central portion of the sliding movable wall (21), which utilizes rollers (rd) on rails (30) and (31), installed on the ground (22) and ceiling (25), sustained by profiles (25*a*). All the modular structure (20) presents a white and opaque tone, as well as a proper lighting (il), which is controlled and proper, according to the test.

In front of the movable wall (21) and coplanar to the rear wall (24) of booth (10), a seat (27) is installed to accommodate the patient (pc) and an optional companion.

The sliding of the movable wall (21) makes up the distance adjustment (d10 between the patient (pc) and the visualization area (21*a*) of the cards (CT), where the minimum distance is equivalent to 38 centimeters and the maximum distance corresponds to 55 or 84 centimeters as accuracy demands according to the patient's features (pc).

In a preferred constructive version, said modular structure (20) presents ideal height (t1), length (c1) and width (I1), designed for accommodation in offices, clinics or similar rooms, and comprises a floor (22), sidewalls (23), a rear wall 24) and ceiling (25), in a way to compose a frontal bay (VF) provided with a frame (26) and where a movable wall (21) is installed, with width (I2) and height (t2) reduced with respect to width (I2') and height (t2') of bay (VF). An opening (23*a*) is provided in one of the side walls (23) liable to receive a hinged door (27) fixed by hinges (db) and provided with a handle (Px).

The visualization area (21*a*) of the sliding wall (21) cards (CT) comprises a rectangular central cut-out (21*b*), from whose outer face a support (21*c*) with 'L' shape is developed, mirrored in a way to cover the cut-off (21*b*), forming an intersection (IT) for the card (CT) assembly. Said support (21*c*) foresees a central hole (21*d*) that, upon the assembly of the card (CT), becomes aligned with the hole (o1) of the same for the professional to visualize the reactions of the patient (pc) who is accommodated in the booth (10).

When this invention is put into practice, it is certain that modifications concerning certain construction details and form are liable to be introduced without deviating from the fundamental principles clearly presented in the claims, it being thus understood that the terminology is not limiting.

What is claimed is:

1. A booth preferred visual acuity test, a booth being operative to quantify visual acuity of a patient, irrespective of the verbal information about the patient (pc), wherein said booth preferred visual acuity test uses Teller cards for the patient, the booth preferred visual acuity test comprising:

an isolated environment (AS) within a modular structure (20) for the patient (pc) to perform the preferred visual acuity test through reading of Teller cards accommodated within a visualization area (21*a*), wherein the cards are laid out in a central portion of a sliding movable wall (21) and wherein the sliding wall has wheels (rd) on rails (30, 31) are installed on the ground (22) and ceiling (25), the modular structure (20) presenting a white and opaque tone, as well as its own lighting (II), controlled and fit according to the test, wherein in front of the movable wall (21) and coplanar to the rear wall (24) of the booth (100) there is installed a seat (28) for accommodation of the patient (pc) and an optional companion;

the movable wall sliding (21) being operative to adjust distance (dl) between the patient (pc) and the visualization area (21*a*) of cards (CI), wherein the distance varies between a minimum distance of 38 centimeters and maximum distance of 84, varying in accordance with the features of the patient (pc) to optimize accuracy.

2. The booth preferred visual acuity test according to claim 1, wherein the modular structure (20) comprises at least one of:

wood, drywall, or PVC.

3. The booth preferred visual acuity test according to claim 1, wherein the modular structure (20) comprises:

ideal height (t'), length (cl) and width (I1) for positioning in offices, clinics or similar rooms, and comprising a ground (22), side walls (23), a rear wall (24) and a ceiling (25), opening up upon a frontal bay (VF) provided with a frame (26), wherein a movable wall (10) is installed, with width (I2) and height (t2) reduced with respect to the width (I2') and height (t2") of bay (VF);

an opening (23*a*) in one of the side walls (23), fixed by hinges (db) and provided with a handle (Px); and a visualization area (21*a*) for viewing the sliding wall (21) cards (CT) comprising a rectangular central cut-off (21*b*), the external face of the visualization area (21*a*) forming an L shape support (21*c*) in a way to cover the cut-off (21*b*), forming an intersection (IT) for an assembly of the card (CT), said cut-off (21*b*) forming a central orifice (21*d*) which, upon the assembly of the card (CT), aligns with the orifice (ol) of the same for the professional to visualize the reactions of the patient (pc), accommodated within the booth (10).

4. The booth preferred visual acuity test according to claim 1, wherein the booth preferred visual acuity test is performed by a professional in an office or a clinic.

\* \* \* \* \*